(12) United States Patent
Toyoda (10) Patent No.: US 8,372,650 B2
(45) Date of Patent: Feb. 12, 2013

(54) SENSING ELEMENT FOR NITROGEN OXIDE MOLECULE SENSING APPARATUS FOR NITROGEN OXIDE MOLECULE AND METHOD FOR SENSING NITROGEN OXIDE MOLECULE

(75) Inventor: Kenji Toyoda, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/432,317

(22) Filed: Mar. 28, 2012

(65) Prior Publication Data

US 2012/0184045 A1 Jul. 19, 2012

Related U.S. Application Data

(63) Continuation of application No. PCT/JP2011/004284, filed on Jul. 28, 2011.

(30) Foreign Application Priority Data

Aug. 5, 2010 (JP) .................................. 2010-175949

(51) Int. Cl.
*G01N 27/04* (2006.01)
*G01N 33/00* (2006.01)

(52) U.S. Cl. .................. 436/116; 422/82.01; 422/82.02; 422/83; 422/88; 422/90; 436/106; 436/149

(58) Field of Classification Search .... 422/82.01–82.02, 422/83, 88, 90; 436/106, 116–118, 133–134, 436/136, 149

See application file for complete search history.

(56) References Cited

U.S. PATENT DOCUMENTS

| | | | |
|---|---|---|---|
| 4,718,991 A * | 1/1988 | Yamazoe et al. ........... 205/785.5 |
| 5,318,912 A | 6/1994 | Silver et al. |
| 5,451,674 A | 9/1995 | Silver et al. |
| 5,603,820 A * | 2/1997 | Malinski et al. .............. 205/781 |
| 5,729,427 A * | 3/1998 | Li et al. .......................... 361/503 |
| 5,980,705 A * | 11/1999 | Allen et al. .................... 205/781 |
| 6,943,054 B2 * | 9/2005 | Bocian et al. .................... 438/99 |
| 7,258,838 B2 * | 8/2007 | Li et al. ......................... 422/68.1 |
| 7,312,100 B2 * | 12/2007 | Bocian et al. .................... 438/99 |
| 7,582,490 B2 * | 9/2009 | Golovchenko et al. .......... 438/10 |
| 7,868,426 B2 * | 1/2011 | Willis et al. .................... 257/618 |
| 2002/0015963 A1 * | 2/2002 | Keen ................................. 435/6 |
| 2004/0120180 A1 * | 6/2004 | Rotenberg et al. ............ 365/151 |
| 2004/0161708 A1 * | 8/2004 | Nagase et al. ................. 430/313 |
| 2004/0235184 A1 * | 11/2004 | Swager ......................... 436/149 |
| 2005/0077192 A1 * | 4/2005 | Yuasa et al. .................... 205/775 |

(Continued)

FOREIGN PATENT DOCUMENTS

JP 5-505871 8/1993
JP 2005-127998 5/2005

OTHER PUBLICATIONS

Di Natale C. et al, Sensor and Actuators B 2007, 121, 238-246.*

(Continued)

*Primary Examiner* — Arlen Soderquist
(74) *Attorney, Agent, or Firm* — Wenderoth, Lind & Ponack, L.L.P.

(57) ABSTRACT

In a sensing element for a nitrogen oxide molecule of the present invention, a sensing portion that is to be bonded to a nitrogen oxide molecule to be sensed is fixed between paired metal electrodes through connecting portions. The sensing portion is a single porphyrin molecule or a single porphyrin derivative molecule each having, as a central metal thereof, iron or cobalt. The connecting portions are each a mercaptophenyleneethynyl group bonded to the single porphyrin molecule or the single porphyrin derivative molecule. Provided are a sensing element for nitrogen oxide molecule, a sensing apparatus for nitrogen oxide molecule, and a method for sensing nitrogen oxide molecule.

4 Claims, 5 Drawing Sheets

U.S. PATENT DOCUMENTS

| | | | |
|---|---|---|---|
| 2005/0084204 A1* | 4/2005 | Zhou et al. | 385/16 |
| 2005/0285275 A1* | 12/2005 | Son et al. | 257/773 |
| 2006/0289313 A1* | 12/2006 | Yuasa et al. | 205/782 |
| 2008/0269486 A1* | 10/2008 | Zhou et al. | 544/250 |
| 2010/0084276 A1* | 4/2010 | Lindsay | 205/93 |
| 2010/0144535 A1* | 6/2010 | Strachan et al. | 505/100 |
| 2010/0184062 A1* | 7/2010 | Steinmuller-Nethl et al. | 435/6 |
| 2011/0056845 A1* | 3/2011 | Stellacci et al. | 205/777.5 |

OTHER PUBLICATIONS

Sedghi, G. et al, Journal of the American Chemical Society 2008, 130, 8582-8583.*

Banerjee, P. et al, ACS Nano 2010, 4, 1019-1025.*

Tagami et al., "Chemical contact promising for coherent transport through tape-porphyrin molecular bridges", e-Journal of Surface Science and Nanotechnology, vol. 1, pp. 45-49, 2003.

Bedioui et al., Design and characterization of chemically modified electrodes with iron (III) porphyrinic-based polymers: Study of their reactivity toward nitrites and nitric oxide in aqueous solution, Analytica Chimica Acta, vol. 341, pp. 177-184, 1997.

Wu et al., "Novel NO Biosensor Based on the Surface Derivatization of GaAs by "Hinged" Iron porphyrins", Angew. Chemical International Education, No. 24, 39, pp. 4496-4500, 2000.

* cited by examiner

SENSING ELEMENT FOR NITROGEN OXIDE MOLECULE SENSING APPARATUS FOR NITROGEN OXIDE MOLECULE AND METHOD FOR SENSING NITROGEN OXIDE MOLECULE

CROSS-REFERENCE TO RELATED APPLICATIONS

This is a continuation application of International Application No. PCT/JP2011/004284, filed Jul. 28, 2011 entitled "Sensing element for gaseous molecule sensing apparatus for gaseous molecule and method for sensing gaseous molecule" and claims priority to Japanese Application No. 2010-175949 filed Aug. 5, 2010, the content of which is incorporated by reference herein.

BACKGROUND OF THE INVENTION

1. Field of the Invention

The present invention relates to a sensing element for a nitrogen oxide molecule, a sensing apparatus for a nitrogen oxide molecule, and a method for sensing a nitrogen oxide molecule.

2. Description of Related Art

Nitrogen oxide (NO) is oxidized in the atmosphere to turn to poisonous nitrogen dioxide. Thus, it is desired to sense the state where NO at a low concentration is present. It is known that NO is a neurotransmitter in living bodies, and fulfills an important function in immunoreaction, blood pressure adjustment, and the like. As described herein, attention has been paid to the sensing of NO for the environment, or the diagnosis of living bodies.

As a conventional NO molecule sensing apparatus, known is an apparatus in which a monolayer of a derivative of a porphyrin molecule (hereinafter abbreviated as FeP) having, as a central metal, an iron atom is used as the gate region of an FET (field effect transistor) (see, for example, Non-Patent Literature 1: D. G. Wu, G. Ashkenasy, D. Shvarts, R. V. Ussyshinkin, R. Naaman, A. hanzar, and D. Cahen, "Angew. Chem. Int. Ed", WILEY-VCH Publisher, May 17, 2000, pp. 4496-4499). A NO molecule is coordinated and bonded to the central metal of FeP, whereby the electronic state of FeP changes. This change in the electronic state causes a change in static electricity of the gate region so that the drain current (concerned) is changed. In such a way, an FET type sensor senses a NO molecule in accordance with a change in the drain current. Non-Patent Literature 1 discloses that the lowest concentration that can be sensed is about 4.1 ppm.

In the meantime, as an apparatus for directly measuring a change in the electronic state of a molecule, known is an apparatus of estimating the electric conduction characteristic of a single molecule junction between electrodes (see, for example, Patent Literature 1: JP-A-2005-127998). This is a molecule-sensing nanosensor having a sensing portion made of bipyridine. When a platinum ion is bonded to the sensing portion, bipyridine is changed into an electroconductive state. The molecule-sensing nanosensor is a sensor of detecting a change in the electronic state of its sensing portion.

Also known is an apparatus of estimating the electric conduction characteristic of a porphyrin molecule junction between electrodes (see, for example, Non-Patent Literature 2: K. Tagami and M. Tsukada "e-Journal of Surface Science and Nanotechnology", Published by the Surface Science Society of Japan, Jun. 30, 2003, pp. 45-49). This reference estimates the electric conduction characteristic of a polymer called tape porphyrin, wherein porphyrin molecules are bonded to each other. In Non-Patent Literature 2, as a functional group bridging tape-porphyrin and electrodes, the following three species are each prepared and their electric conduction characteristic are compared with each other: a mercaptophenyl group, a mercaptophenylenevinyl group and a mercaptophenyleneethynyl group. In tape-porphyrin, even when changing its functional group to the above groups, the electric conduction characteristic is not very largely changed among the apparatuses using these species.

SUMMARY OF THE INVENTION

However, the above-mentioned conventional FET type sensor structure has the following problem; in this structure, a change in the electronic state of its porphyrin molecule modulates, through the insulating film of the gate, the channel region; thus, the lowest concentration that can be sensed is several parts per million, and the performance of the sensor cannot be easily improved up from this level.

Against this structure, a method as described in Patent Literature 1 is conceivable, in which a change in the electronic state of a single molecule junction between electrodes is directly measured, and thereby to improve the sensitivity. However, under the present situation, a sufficient result has not been obtained yet about the sensitivity improvement.

Not only about NO but also about carbon monoxide (CO) or oxygen ($O_2$), a sensing method giving a higher sensitivity is required.

In order to solve the problems described, an object of the present invention is to provide a sensing element for a nitrogen oxide molecule, a sensing apparatus for a nitrogen oxide molecule, and a method for sensing nitrogen oxide molecule.

The inventors have found out that in a process for measuring directly a change in the electronic state of a porphyrin molecule, sensing NO with a high sensitivity can be possible by controlling a functional group through which a molecule of the porphyrin molecule and each electrode are connected to each other, thus, the invention has been completed.

Accordingly, the sensing element for a nitrogen oxide molecule according to the present invention includes a pair of metal electrodes, connecting portions, and a sensing portion to which the nitrogen oxide molecule to be sensed is bonded, the sensing portion being fixed between the paired metal electrodes through the connecting portions, wherein the sensing portion is a single porphyrin molecule or a single porphyrin derivative molecule each having, as a central metal thereof, iron or cobalt, and the connecting portions are each a mercaptophenyleneethynyl group bonded to the selected single porphyrin molecule or single porphyrin derivative molecule.

The sensing apparatus for a nitrogen oxide molecule according to the invention includes a sensor having the sensing element for nitrogen oxide molecule and a substrate that holds the sensing element for nitrogen oxide molecule; a filter unit for removing any gaseous molecule other than the nitrogen oxide molecule to be sensed; and an electric current measuring unit for measuring a change in electric current value that passes through the sensing element for nitrogen oxide molecule.

The method for sensing a nitrogen oxide molecule according to the invention uses the sensing apparatus for nitrogen oxide molecule.

The invention makes it possible to increase a change in electric current generated when a nitrogen oxide molecule to be sensed is bonded to the porphyrin molecule, so that the nitrogen oxide molecule can be sensed with a high sensitivity.

DETAILED DESCRIPTION OF THE PREFERRED EMBODIMENTS

With reference to the drawings, embodiments of the present invention will be described hereinafter.

Sensing Element for Nitrogen Oxide Molecule:

The sensing element for a nitrogen oxide molecule of the invention includes a pair of metal electrodes, connecting portions, and a sensing portion to which the nitrogen oxide molecule to be sensed is bonded, and the sensing portion is fixed between the pair of metal electrodes through the connecting portions, and the sensing portion is a single porphyrin molecule or a single porphyrin derivative molecule having, as a central metal thereof, iron or cobalt, and the connecting portions are each a mercaptophenyleneethynyl group bonded to the single porphyrin molecule or the single porphyrin derivrative molecule.

Figure 1:
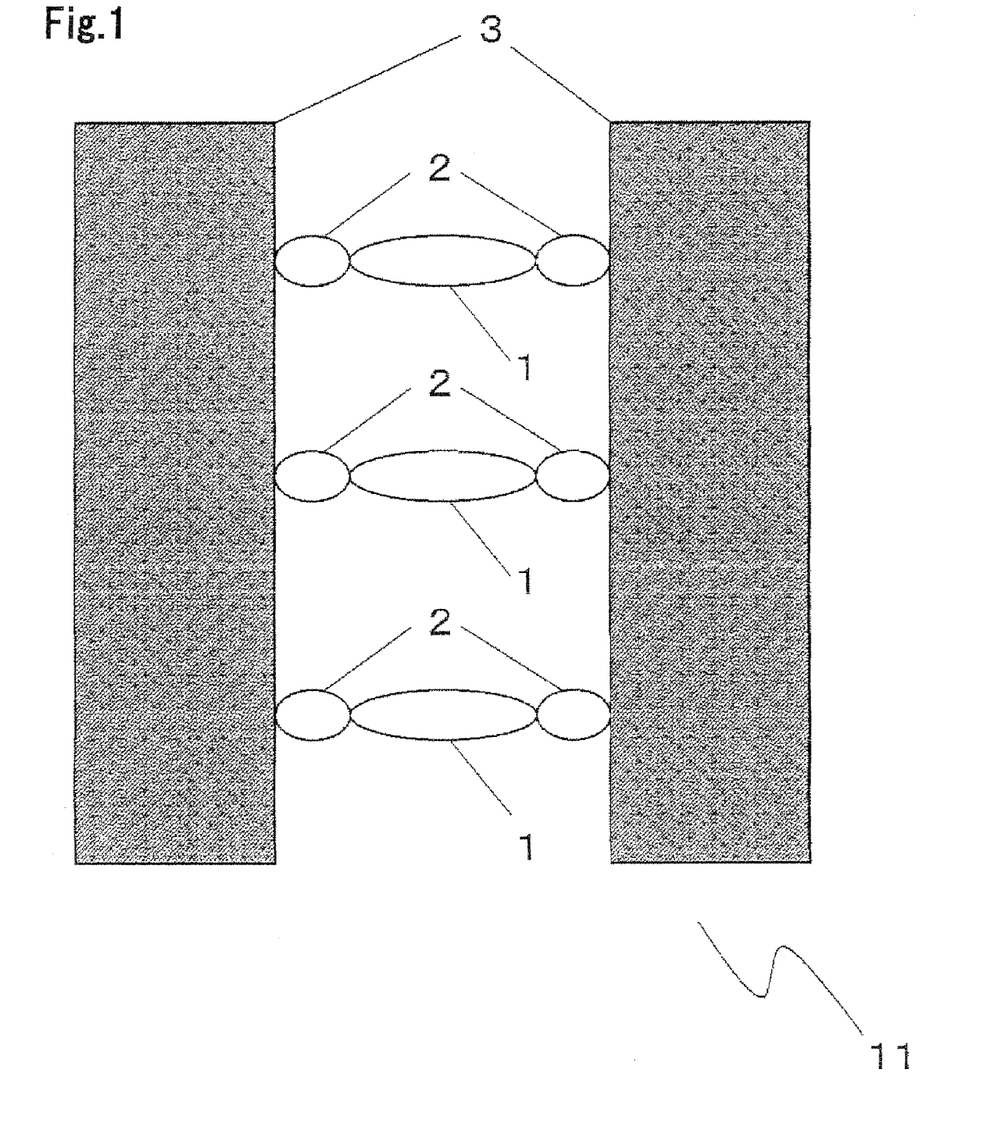
FIG. 1 is a schematic plan view illustrating an example of the structure of the sensing element for nitrogen oxide molecule of the invention.

FIG. 1 is a schematic plan view illustrating an example of the structure of the sensing element for nitrogen oxide molecule of the invention.

In a sensing element for nitrogen oxide molecule 11, a sensing portion 1 to which a nitrogen oxide molecule to be sensed is bonded is fixed between a pair of metal electrodes 3 and 3 through connecting portions 2 and 2.

The sensing portion 1 includes a single porphyrin molecule or single porphyrin derivative molecule that has a central metal which is bonded to the nitrogen oxide molecule to be sensed. The central metal is iron or cobalt.

Here, the single porphyrin molecule denotes, as represented by following chemical formula 1, one porphyrin molecule that is not combined with one or more other porphyrin molecules, so as not to form a dimer or the like, and $R_1$ to $R_{12}$ are each a hydrogen atom.

[Chemical formula 1]

On the other hand, the single porphyrin derivative molecule is a single porphyrin having a substituent. In connection with the substituent, $R_1, R_2, R_4, R_5, R_7, R_8, R_{10}$ and $R_{11}$ in the above chemical formula each independently represent a hydrogen atom, a linear alkyl group having 1 to 3 carbon atoms, or a phenyl group which may have, as a substituent, a linear alkyl group having 1 to 3 carbon atoms; about one pair out of a pair of $R_3$ and $R_9$, and a pair of $R_6$ and $R_{12}$, the paired elements thereof each represent a phenyl group which may have a linear alkyl group having 1 to 3 carbon atoms, —$CH_2$—$CH_2$—$CH_3$, —CH=CH—$CH_3$, —C≡C—$CH_3$, —$CH_2$—$CH_2$-Ph, —CH=CH-Ph, or —(C≡C-Ph)n- wherein n is a natural number from 1 to 50, wherein Ph represents a phenyl group which may have, as a substituent, a linear alkyl group having 1 to 3 carbon atoms; and about the other pair, the paired elements thereof each represent a hydrogen atom. Preferably, $R_1, R_2, R_4, R_5, R_7, R_8, R_{10}$, and $R_{11}$ each represent a hydrogen atom, and about one pair out of the pair of $R_3$ and $R_9$, and the pair of $R_6$ and $R_{12}$, the paired elements thereof each represent a phenyl group which may have, as a substituent, a linear alkyl group having 1 to 3 carbon atoms, —$CH_2$—$CH_2$—$CH_3$, —CH=CH—$CH_3$, —C≡C—$CH_3$, —$CH_2$—$CH_2$-Ph, —CH=CH-Ph, or —(C≡C-Ph)n- wherein n is a natural number from 1 to 50. More preferably, about one pair out of the pair of $R_3$ and $R_9$, and the pair of $R_6$ and $R_{12}$, the paired elements thereof are each —$CH_2$—$CH_2$-Ph, —CH=CH-Ph, or —(C≡C-Ph)n- wherein n is a natural number from 1 to 50.

The connecting portions are linker molecules that are bonded to the paired metal electrode, respectively, thereby having a function of fixing the sensing portion between the paired electrodes. For each of the connecting portions, used is a mercaptophenyleneethynyl group, which may be referred to as an MPE group hereinafter, that is bonded to the above-mentioned single porphyrin molecule or single porphyrin derivative molecule. The mercaptophenyleneethynyl group may have, in the phenylene group thereof, a substituent. The substituent may be a linear alkyl group having 1 to 3 carbon atoms. The phenylene group preferably has no substituent.

The metal electrodes used in the invention are paired electrodes having an interval being matched with the molecular length of the single molecule, and may be nano-gap electrodes having a gap width in the order of nanometers. In the invention, a gap width being matched with the molecular length of the single porphyrin molecule or single porphyrin derivative molecule is used. The lower limit of the gap width between the electrodes is about 2.5 nm, which is a minimum working size obtained by electron beam exposure apparatuses. The upper limit is about 100 μm. The material of the metal electrodes may be gold, copper, or aluminum, and is preferably gold.

The sensing element may be produced by, for example, a method described below.

1. Production of Nano-Gap Electrodes

An electrode layer of gold having a predetermined film thickness is formed on a substrate, for example, a silicon substrate by vapor deposition. Thereafter, in accordance with a method disclosed in JP-A-2006-128438, an electron beam exposure apparatus is used to pattern the electrode layer, thereby forming nano-gap electrodes having a predetermined electrode width and a predetermined gap width. According to this method, gap electrodes having a gap width of about 2.5 nm can be formed.

2. Bonding of Molecules to be Sensed to the Electrodes

Next, a surface of the gold electrode layer is washed with a piranha solution, and then the substrate is immersed in a solution containing molecules to be sensed (concentration: about 1 nmol/L in a solvent of NaOMe). As thiol groups (—SH) are very active, when the MPE groups are left as they are, unfavorable disulfide groups are formed. In order to prevent the unfavorable disulfide group formation, TIPS groups, which are silyl type protecting groups, may be used. When the solution is controlled from alkalinity to acidity, the thiol groups are deprotected.

In a case where NO is introduced into the gaseous molecule sensing element of the invention while a predetermined voltage is applied thereto, a more remarkable increase in electric current value is recognized than conventional method even when the concentration of NO is low. As a result, NO can be sensed with higher sensitivity. The concentration of NO molecules that can be sensed is from 0.02 to 20 ppm, preferably from 0.04 to 20 ppm.

Note that the above description has been made about the case where the gaseous molecules to be detected are NO molecules; however, the sensing element for nitrogen oxide molecule of the invention may be used to sense CO or $O_2$ for the following reason: the central metal of the single porphyrin molecule or the single porphyrin derivative molecule is iron or cobalt; and CO or $O_2$ has unpaired electrons so as to be bonded to the central metal in the same way as NO. The sensing element for nitrogen oxide molecule of the invention may be used for any gaseous molecule having unpaired electrons except for NO, CO and $O_2$.

Sensing Apparatus for Nitrogen Oxide Molecule:

The sensing apparatus for nitrogen oxide molecule of the invention includes: at least a sensor having the sensing element for nitrogen oxide molecule of the invention, and a substrate that holds the sensing element for nitrogen oxide molecule; a filter unit for removing any gaseous molecule other nitrogen oxide molecule to be sensed; and an electric current measuring unit for measuring a change in electric current value that passes through the sensing element for nitrogen oxide molecule.

Figure 2:
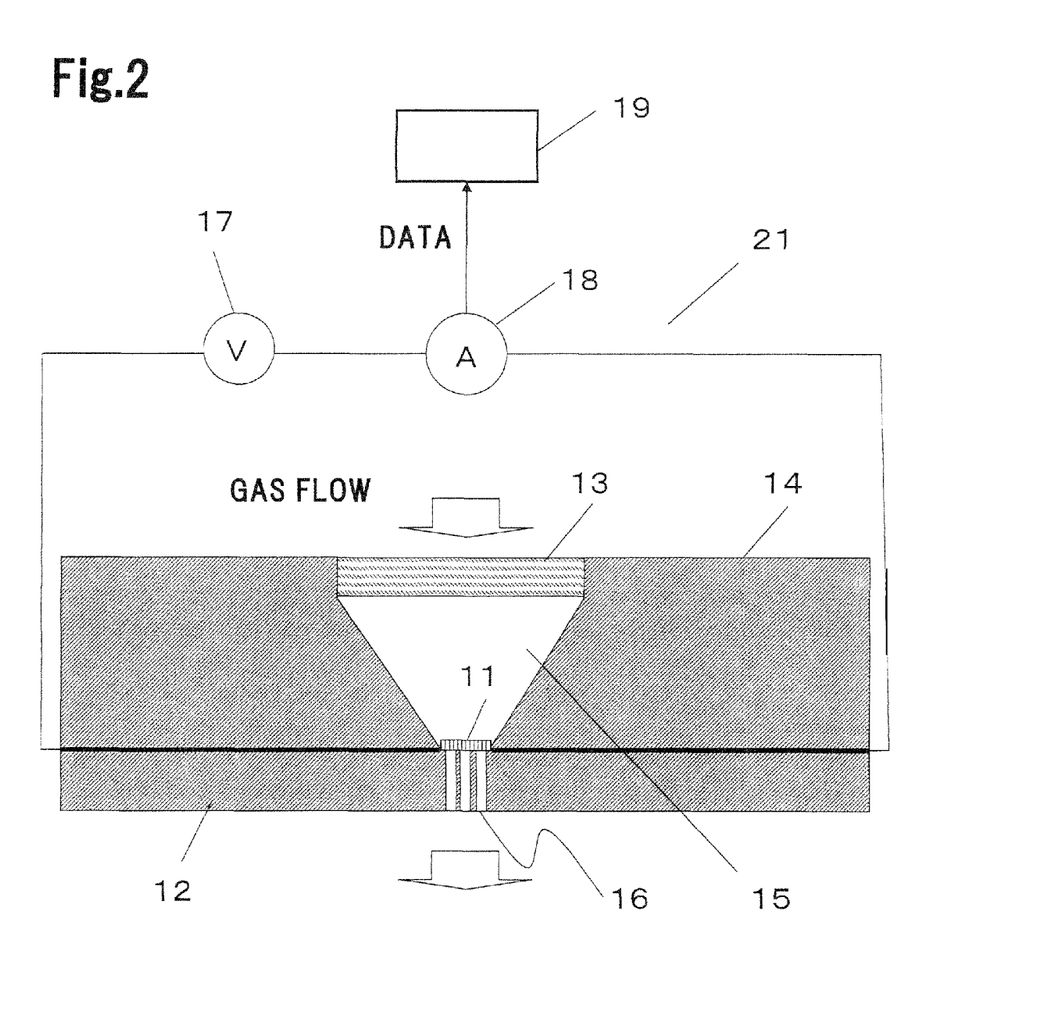
FIG. 2 is a schematic view illustrating an example of the structure of the sensing apparatus for nitrogen oxide molecule of the invention.

FIG. 2 is a schematic view illustrating an example of the structure of the sensing apparatus for nitrogen oxide molecule of the invention.

A sensing apparatus for nitrogen oxide molecule 21 has a sensor 12, a filter unit 13 for removing gaseous molecules other than nitrogen oxide molecule to be sensed, a DC source 17 for applying voltage to a sensing element for nitrogen oxide Molecule 11, an electric current measuring unit 18 for measuring a change in electric current value that passes through the sensing element for nitrogen oxide molecule 11, and a data processing unit 19 for determining the concentration of the gas to be sensed on the basis of data from the electric current measuring unit 18. The sensor 12 includes the sensing element for nitrogen oxide molecule 11, and a substrate 14 that holds the sensing element for nitrogen oxide molecule 11.

For the substrate 14, for example, silicon or sapphire may be used. FIG. 2 shows an example in which the substrate is etched to form a depression 15 and further the sensing element for nitrogen oxide molecule 11 is arranged on the bottom of the depression 15. Over the sensing element for nitrogen oxide molecule 11, the filter unit 13 is removably mounted to the substrate 14 so as to cover the depression 15, and an exhaust hole 16 having one or more through holes reaching a rear surface of the substrate is provided at the bottom of the depression 15. The gas to be sensed passes through the filter unit to be shifted inside the depression, then reaches the sensing element for nitrogen oxide molecule, and thereafter, the gas is discharged from the substrate 14 through the exhaust hole 16. The depression 15 preferably has a V-shaped cross section. The reason is the gas to be sensed having passed through the filter unit 13 can be converged and can reach the sensing element for nitrogen oxide molecule.

Although FIG. 2 shows a structure in which the filter unit is arranged to be integrated with the substrate, the filter unit needs only to have a function of removing gaseous molecules other than the nitrogen oxide molecule to be sensed, and thus the filter unit may be arranged separately from the substrate. For example, it may be possible to provide a pipe having a filter and arrange the pipe so that an outlet of the pipe is situated near the sensing element for nitrogen oxide molecule.

For the filter unit, a material having a function of removing gaseous molecules other than the nitrogen oxide molecule to be sensed from the gas to be measured is used. When the gaseous molecules to be sensed are NO molecules, for example, it is preferable to use an activated carbon having an average pore diameter of 2 nm. The activated carbon can remove gas components other than NO (such as nitrogen dioxide, carbon dioxide, carbon monoxide, and oxygen). However, NO, which does not have an affinity to the surface of the activated carbon, passes through the filter without being removed. The average pore diameter of the activated carbon may be measured by the gas adsorption method.

When the target to be sensed is CO molecules or $O_2$ molecules, a gas isolating membrane may be used through which only CO molecules or $O_2$ molecules can be passed. For example, a gas isolating membrane may be used which is made of a polymeric gel described in JP-A-7-275672. For example, in order to allow only CO to pass through the filter unit, a polymeric gel containing $Cu(NH_4)^{2+}$ as a carrier (affinitive material that can interact with specific gas molecules) may be used for the filter unit. Further, in order to allow only $O_2$ to pass selectively through the filter unit, a polymeric gel containing $Co(NH_4)^{2+}$ as a carrier may be used for the filter unit.

Sensing Method for Nitrogen Oxide Molecule:

The method for sensing nitrogen oxide molecule of the invention is not particularly limited as far as the sensing apparatus for nitrogen oxide molecule of the invention is used. The method preferably includes at least the step of preparing a calibration curve by use of a standard gas (step 1), the step of desorbing the adsorbed standard gas (step 2), and the step of determining the concentration of a gas to be sensed (step 3).

Figure 3:
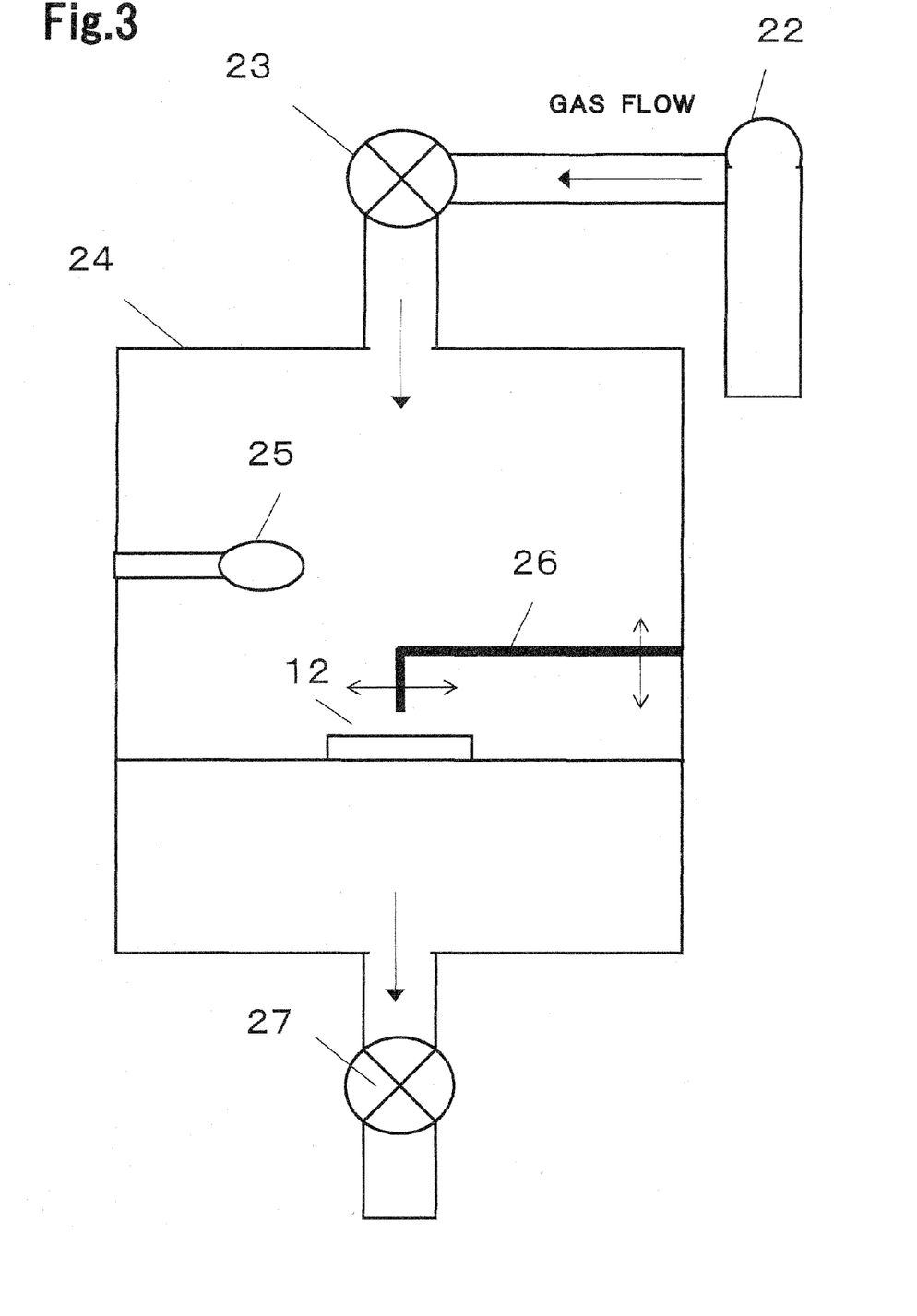
FIG. 3 is a schematic view illustrating an example of an apparatus used in the method for sensing nitrogen oxide molecule of the invention.

FIG. 3 is a schematic view to explain the method for sensing nitrogen oxide molecule of the invention. An apparatus illustrated therein is used in steps 1 and 2. A sensor 12 is arranged in an airtight container 24. From a gas cylinder 22 containing a standard gas, the standard gas is introduced through a supply valve 23 into the airtight container 24, and then discharged from an exhaust value 27. Reference numeral 26 represents a manipulator, and the manipulator is used to detach a filter unit fitted to the sensor 12. Reference numeral 25 represents a white lamp for desorbing the standard gas.

Hereinafter, with reference to FIGS. 2 and 3, a description will be made about the sensing method in the case of using NO molecules as gaseous molecules to be sensed.

1. Step 1

In the present step, a standard gas (NO in Ar as a base gas; NO concentration; 10 ppm) is used to determine a calibration curve.

The sensor 11 is arranged in the airtight container 24. Next, the gas cylinder 22 containing the standard gas is connected to a pipe joined to the supply valve 23. Next, the supply valve 23 and the exhaust valve 27 are opened, so that the standard gas is adsorbed on the sensor. At this time, data on the electric current in response to the standard gas which is measured by the electric current measuring unit 18 is transmitted to the data processing unit 19. Next, in the data processing unit 19, a coefficient A is determined from the concentration of the standard gas and the data on the electric current measured in accordance with the following equation (1):

$$\Delta I = A \times C \tag{1}$$

wherein $\Delta I$ represents an increase in the electric current (A); C, the concentration (ppm); and A, the coefficient (A/ppm).

After the termination of the measurement, the supply valve 23 and the exhaust valve 27 are closed.

2. Step 2

In the present step, the adsorbed standard gas is desorbed.

The manipulator 26 is operated to detach the filter unit 13 of the sensor 12. Next, the exhaust valve 27 is opened and the white lamp 25 giving a predetermined irradiance or more (for example, about 200 J/m²s or more) is switched on to radiate light rays onto the sensor 12 over about 5 minutes. Thus, it is possible to desorb the standard gaseous molecules adsorbed on the central metals of the porphyrin rings in step 1. After the radiation of the rays from the lamp, the white lamp 25 is switched off. Finally, the manipulator 26 is operated to return the filter unit to an original position, and then the exhaust valve 27 is closed.

3. Step 3

In the present step, the concentration of the gas to be sensed is determined.

The sensor 12 is taken out from the airtight container 24. Next, the target gas to be sensed is sensed by means of the sensor 12. At this time, data on the electric current in response to the gas to be sensed which is measured by the electric current measuring unit 18 is transmitted to the data processing unit 19. In the data processing unit 19, using the coefficient A obtained in step 1 and the data on the value of the increased electric current, the concentration of the gas to be sensed is determined in accordance with the above-mentioned equation (1).

EXAMPLES

Example 1

For each of sensing portions in the present example, used was a single porphyrin derivative molecule represented by a chemical formula (2) illustrated below, which has a central metal (the compound will be referred to as the compound 1 hereinafter). For each of connecting portions therein, a mercaptophenyleneethynyl group was used. For the central metal, iron was used.

[Chemical formula 2]

Synthesis of Compound 1:

The compound 1 was synthesized by use of the Rothemund method using pyrrole, an aldehyde having an MPE group, and an aldehyde having a phenyleneethynyl group.

Formation of Sensing Element for Nitrogen Oxide Molecule:

An electrode layer of gold having a film thickness of about 50 μm was formed on a silicon substrate by vapor deposition. Thereafter, in accordance with the method disclosed in JP-A-2006-128438, an electron beam exposure apparatus was used to pattern the electrode layer, thereby forming nano-gap electrodes having an electrode width of about 50 μM and a gap width of about 2.5 nm.

A surface of the gold electrode layer was washed with a piranha solution, and then the substrate was immersed in a solution containing the compound 1 (concentration: about 1 nmol/L in a solvent of NaOMe). For reference, thiol groups (—SH) are very active; thus, when the MPE groups are kept as they are, unfavorable disulfide groups are formed. For the prevention thereof, triisopropylsilyl (TIPS) groups, which are silyl type protecting groups, were used. When the solution was controlled from alkalinity to acidity, the thiol groups were each deprotected. At this time, a hydrogen atom was eliminated from the thiol group at a terminal of each of the molecules so that its sulfur atom was bonded to the surface of gold. Thereafter, the substrate was taken out from the solution, and dried by use of a nitrogen gun or the like. In this way, a sensing element for nitrogen oxide molecule was formed.

Electroconductivity of Sensing Element for Nitrogen Oxide Molecule:

A voltage of 0.4 V was applied to the electrodes of the formed sensing element across the electrodes so that an electric current of about 120 mA was obtained. Note that the voltage to be applied may be appropriately set as far as the sensing element is not damaged.

Sensing Characteristic Evaluation:

The formed sensing element was integrated into the sensor 12 in FIG. 2, and a standard gas (10 ppm NO in Ar as a base gas) was diluted with Ar gas to vary the concentration of NO therein. In this way, a change in the value of electric current therein was measured in the range that the NO concentration was from 0.04 to 20 ppm. The measurement was made at room temperature while a voltage of 0.4 V was applied across the electrodes.

Figure 4:
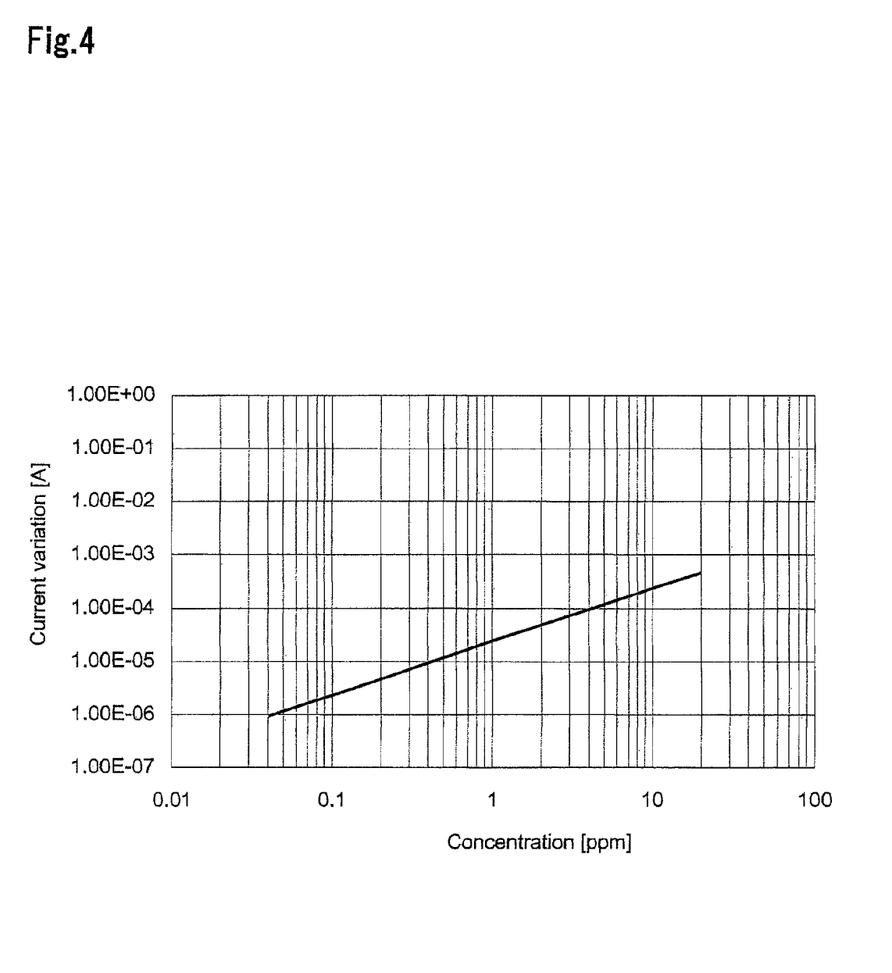
FIG. 4 is a graph showing a relationship between the nitrogen oxide molecule concentration of a sensing element for nitrogen oxide molecule in Example 1, and the current variation thereof.

The results are shown in FIG. 4. In FIG. 4, its vertical axis represents the current variation (A), and its transverse axis represents the NO concentration (ppm). The current variation is a difference between the current value after the sensing of the NO molecules, and that before the sensing. In FIG. 4, the absolute value thereof is shown. Upon sensing the NO molecules in the invention, the measured current value was decreased; thus, the current variation was a decreasing amount. As illustrated in FIG. 4, within the concentration range of 0.04 to 20 ppm, the current variation was increased in proportion to the NO concentration. At a concentration of 0.04 ppm, a current variation of about 0.9 μA was obtained. As described herein, a sufficient current variation was observed even when the NO concentration was 0.04 ppm, which was a low concentration that had not been reported up to this time. Thus, it can be verified that this invention makes it possible to sense NO with a high sensitivity. In the present example, the value of the inclination A of the calibrating curve in FIG. 4 was $2.36 \times 10^{-5}$ A/ppm.

Comparative Example 1

For each of sensing portions in the present comparative example, used was a single porphyrin derivative molecule represented by a chemical formula (3) illustrated below, which has a central metal (the compound will be referred to as the compound 2 hereinafter). For each of connecting portions therein, a mercaptophenylenevinyl group, which may be referred to as an MPV group hereinafter, was used. For the central metal M, iron was used.

[Chemical formula 3]

Synthesis of Compound 2:

The compound 2 was synthesized by use of the Rothemund method using pyrrole, an aldehyde having an MPV group, and an aldehyde having a phenylenevinylene group.

Formation of Sensing Element for Nitrogen Oxide Molecule:

A sensing element for nitrogen oxide molecule was formed in the same way as in Example 1 except that a solution containing the compound 2 was used.

Electroconductivity of Sensing Element for Nitrogen Oxide Molecule:

In the sensing element of the comparative example, at an applied voltage of 0.4 V, an electric current of about 1.1 mA was obtained. As compared with that in Example 1, the electric current in the present example was an electric current of about one hundredth of the value obtained in Example 1. Thus, it was understood that the sensing element of the present example was higher in resistance than that of Example 1.

Sensing Characteristic Evaluation:

The formed sensing element was integrated into the sensor 11 in FIG. 2, and then the concentration of NO was then varied in the same way as in Example 1 to measure a change in the value of electric current in the sensing element.

Figure 5:
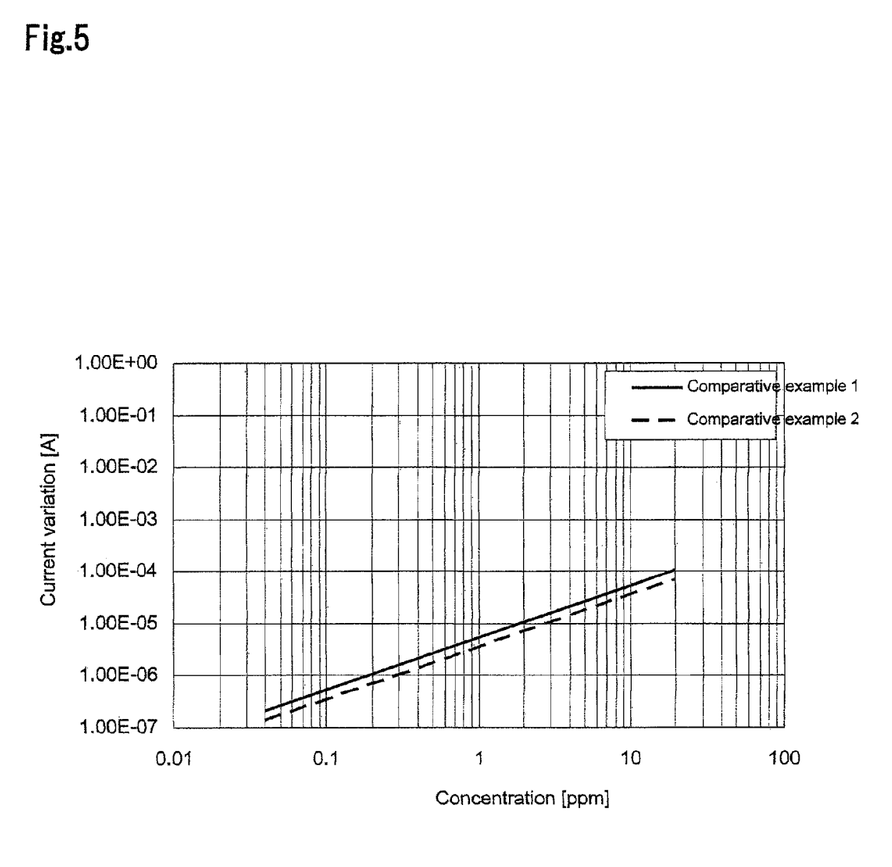
FIG. 5 is a graph showing a relationship between the nitrogen oxide molecule concentration of a sensing element for nitrogen oxide molecule in each of Comparative Examples 1 and 2, and the current variation thereof.

As illustrated in FIG. 5, within the concentration range of 0.04 to 20 ppm, the current variation was increased linearly in proportion to the NO concentration. At a concentration of 0.04 ppm, a current variation of about 0.2 μA was obtained. This value was a value of about a quarter of the value (0.9 μA) obtained in Example 1.

Comparative Example 2

For each of sensing portions in the present comparative example, used was a single porphyrin derivative molecule represented by a chemical formula (4) illustrated below, which has a central metal (the compound will be referred to as the compound 3 hereinafter). For each of connecting portions therein, a mercaptobiphenyl group, which may be referred to as an MBP group hereinafter, was used. For the central metal M, iron was used.

[Chemical formula 4]

Synthesis of Compound 3:

The compound 3 was synthesized by use of the Rothemund method using pyrrole, an aldehyde having an MBP group, and an aldehyde having a phenyl group.

Formation of Sensing Element for Nitrogen Oxide Molecule:

A sensing element for nitrogen oxide molecule was formed in the same way as in Example 1 except that a solution containing the compound 3 was used.

Electroconductivity of Sensing Element for Nitrogen Oxide Molecule:

In the sensing element, at an applied voltage of 0.4 V, an electric current of about 0.57 mA was obtained. As compared with that in Example 1, the electric current in this example was an electric current of about one two-hundredth of the value obtained in example 1. Thus, it was understood that the sensing element of the example was higher in resistance than that of Example 1.

Sensing Characteristic Evaluation:

The formed sensing element was integrated into the sensor 11 in FIG. 2. and the concentration of NO was then varied in the same way as in Example 1 to measure a change in the value of electric current in the sensing element.

As illustrated in FIG. 5, within the concentration range of 0.04 to 20 ppm, the current variation was increased linearly in proportion to the NO concentration. At a concentration of 0.04 ppm, a current variation of about 0.1 μA was obtained. This value was a value of about one eighth of the value (0.9 μA) obtained in Example 1.

Comparative Example 3

For each of sensing portions in the present comparative example, used was a single porphyrin derivative molecule represented by a chemical formula (5) illustrated below, which has a central metal (the compound will be referred to as the compound 4 hereinafter). For each of connecting portions therein, a mercaptophenyl group, which may be referred to as an MP group hereinafter, was used. For the central metal M, iron was used.

[Chemical formula 5]

Synthesis of Compound 4:

The compound 4 was synthesized by use of the Rothemund method using pyrrole, an aldehyde having a mercaptophenyl group, and an aldehyde having a phenyl group.

Formation of Sensing Element for Nitrogen Oxide Molecule:

A sensing element for nitrogen oxide molecule was formed in the same way as in Example 1 except that a solution containing the compound 4 was used.

Electroconductivity of Sensing Element for Nitrogen Oxide Molecule:

In the sensing element, at an applied voltage of 0.4 V, an electric current of about 0.042 mA was obtained.

Sensing Characteristic Evaluation:

The formed sensing element was integrated into the sensor 11 in FIG. 2, and a measurement was made in the same way as in Example 1. However, even when the concentration of NO was varied, the value of electric current in the sensing element was not changed.

The above-mentioned results are shown in Table 1.

TABLE 1

|  | Connecting portions | Electric current (mA) | Current variation (μA) at NO concentration of 0.04 ppm |
|---|---|---|---|
| Example 1 | MPE group | 120 | 0.9 |
| Comparative Example 1 | MPV group | 1.1 | 0.2 |
| Comparative Example 2 | MBP group | 0.57 | 0.1 |
| Comparative Example 3 | MP group | 0.042 | Unable to be measured |

When the MPE groups were used as the connecting portions, the sensing element was largely improved in electroconductivity than when the MPV groups or the MBP groups were used. Furthermore, the electric current variation in the case of the MPE groups caused by the bonding of NO was remarkably improved by one or more orders of magnitude than in the case of the MPV groups or the MBP groups. The improvement of the electric current variation can suppress a noise effect when sensing NO molecules.

As described above, Non-Patent Literature 2 described above does not disclose that in the case of tape porphyrin, a large difference is generated in electroconductivity among the cases of the MPE groups, MPB groups, and the MPV groups. The following is an advantageous effect peculiar to the present invention: the use of an MPE group in each connecting region for a single porphyrin molecule or single porphyrin derivative molecule can bring a remarkable increase of electroconductivity and NO sensing with a high sensitivity.

The reason why NO can be sensed with a high sensitivity would be that when the MPE group is used for each of the connecting portions, the twist angle between the $\pi$ plane of each of the porphyrin rings and the $\pi$ plane of the MPE group is zero degree so that a wide $\pi$ conjugated plane is formed, whereby the electric connection between the porphyrin ring and the electrodes becomes good. By contrast, when the MPV or MBP group is used for each of the connection regions, the sensor is lower in electroconductivity than when the MPE group is used, so that an increase in the electric current value caused by the bonding of NO is also small. The twist angle between the $\pi$ plane of the porphyrin ring and the $\pi$ plane of the MPB group is 66.7 degrees, and the twist angle between the $\pi$ plane of the porphyrin ring and the $\pi$ plane of the MPV group is 52.9 degrees, and therefore, in each of these cases, the twist angle is larger than in the case of the MPE group. From this matter, it can be considered that the following fact contributes to the electric connection between the porphyrin ring and the electrodes: the fact that the $\pi$ plane of each of the connecting portions is not twisted from the $\pi$ plane of the porphyrin ring. For a single porphyrin derivative other than that used in Example 1, if this single porphyrin derivative has a flat structure, the use of the MPE group for each connecting region can bring an improvement in electric connection between the porphyrin ring and the electrodes, because the $\pi$ plane of the MPE group is not twisted from that of the porphyrin ring. The twist angles are each a value based on quantum chemical calculation.

Furthermore, an effect of the molecular length onto the electroconductivity should be considered. When the MP group is used, the total length of each of the sensing portions and the connecting portions (concerned) is shorter than the gap width (about 2.5 nm) between the electrodes; thus, it can be considered that the electrodes cannot be bridged through the sensing portion and the connecting portions. However, in the case of the MBP group, which is longer in molecular length than the MPE group, it appears that the tunnel conduction is decreased to lower the electroconductivity. Note that according to quantum chemical calculation, the molecular length of the MPE group is 2.6 nm; that of the MPV group, 2.5 nm; that of the MBP group, 3.0 nm; and that of the MP group, 2.1 nm.

Furthermore, in case of phthalocyanine, which is a similar $\pi$ conjugated molecule with porphyrin, it is considered that the tunnel conduction is decreased and a sufficient property cannot be obtained, because phthalocyanine is larger in molecular size than porphyrin. It is therefore necessary to use a porphyrin molecule as each sensing portion in order to function as an NO molecule sensing element.

Industrial Applicability

The sensing element for nitrogen oxide molecule of the invention is useful for a gas sensing apparatus for sensing NO, CO or $O_2$ with a high sensitivity.

What is claimed is:

1. A sensing element for a nitrogen oxide molecule, comprising:
   a pair of metal electrodes;
   a connecting portions; and
   a sensing portion to which the nitrogen oxide molecule to be sensed is bonded, the sensing portion being fixed between the pair of metal electrodes through the connecting portions,
   wherein the sensing portion is a single porphyrin molecule or a single porphyrin derivative molecule each having, as a central metal thereof, iron or cobalt, and the connecting portions are each a mercaptophenyleneethynyl group bonded to the selected single porphyrin molecule or single porphyrin derivative molecule.

2. A sensing apparatus for a nitrogen oxide molecule, comprising:
   a sensor having the sensing element for nitrogen oxide molecule according to claim 1 and a substrate that holds the sensing element for nitrogen oxide molecule;
   a filter unit for removing any gaseous molecule other than the nitrogen oxide molecule to be sensed; and
   an electric current measuring unit for measuring a change in electric current value that passes through the sensing element for nitrogen oxide molecule.

3. The sensing apparatus for nitrogen oxide molecule according to claim 2, wherein an activated carbon having an average pore diameter of 2 nm is used for the filter unit.

4. A method for sensing a nitrogen oxide molecule, the method comprising contacting the sensing apparatus of claim 2 with a sample and sensing nitrogen oxide molecules in the sample.

\* \* \* \* \*